United States Patent [19]

Robinson

[11] 4,157,664

[45] Jun. 12, 1979

[54] LIQUID SAMPLING DEVICE

[76] Inventor: Louise J. Robinson, 4120 Foxford Rd., Charlotte, N.C. 28215

[21] Appl. No.: 947,410

[22] Filed: Oct. 2, 1978

[51] Int. Cl.² ............................................... G01N 1/12
[52] U.S. Cl. ............................................... 73/425.4 R
[58] Field of Search .......... 73/421 R, 421 B, 425.4 R, 73/425.6

[56] References Cited

U.S. PATENT DOCUMENTS 3,349,624   10/1967   Fraga ............................. 73/425.4 R

FOREIGN PATENT DOCUMENTS 481312   2/1952   Canada ...................................... 73/425.4

Primary Examiner—S. Clement Swisher

Attorney, Agent, or Firm—Bell, Seltzer, Park & Gibson

[57] ABSTRACT

A sampling device for obtaining a specimen of liquid from a remote location within a large volume or body thereof. The device includes two telescopically disposed receptacles, which form a closed container and which slideably move between closed and open positions. A rapid pull of a line connected to one receptacle will cause the receptacles to separate to the open position as a result of drag forces induced on the other receptacle, and thereby, operation at selective depths and independent of gravitational forces is possible. Furthermore, biasing elements urge the receptacles toward the closed position so that the device can be cast to the desired location and retrieved without allowing undesired liquid to enter the container or the procured sample to escape.

13 Claims, 5 Drawing Figures

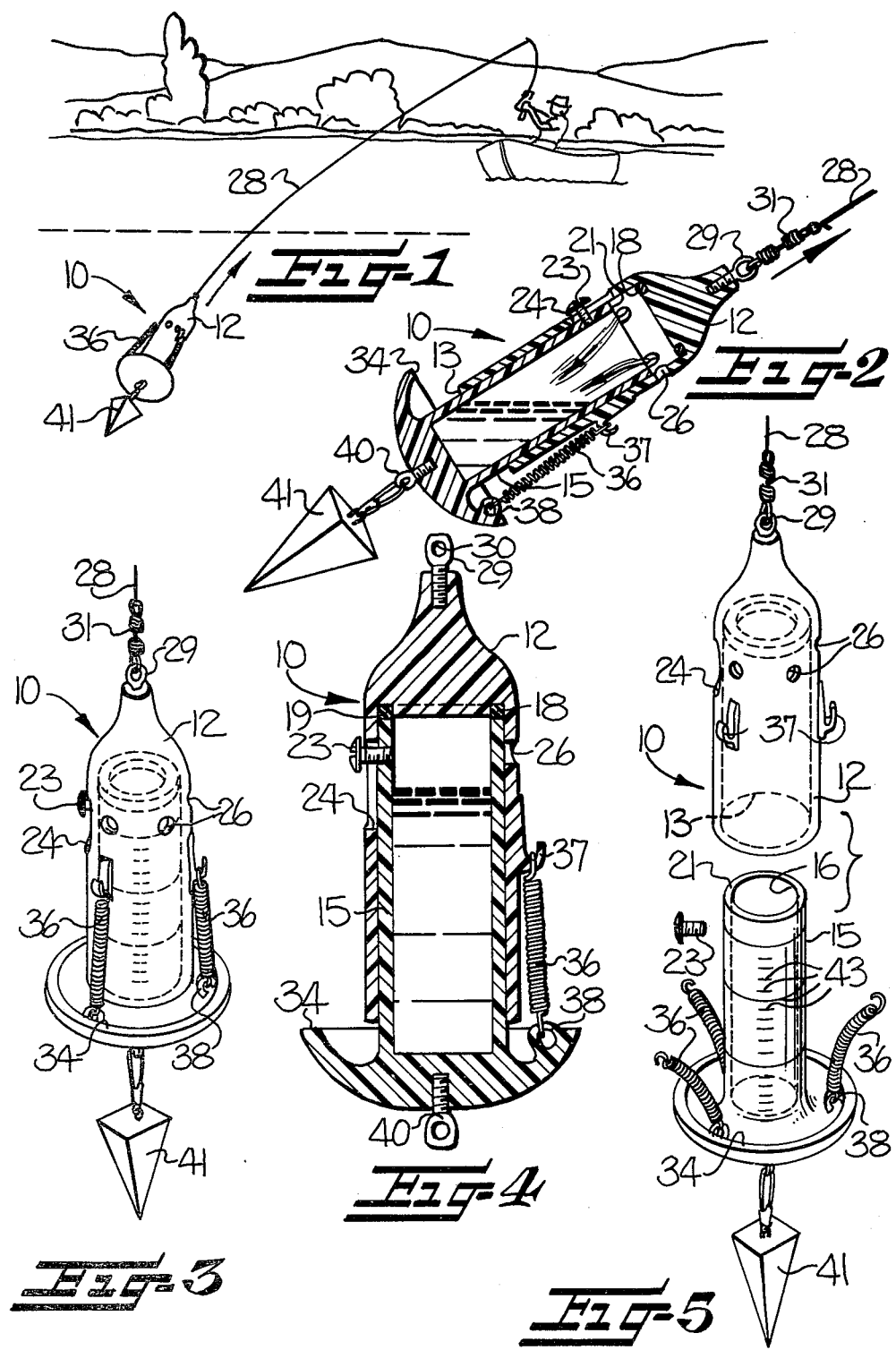

LIQUID SAMPLING DEVICE

FIELD OF THE INVENTION

The present invention relates to a device for obtaining a sample or specimen of liquid from a large volume thereof and more specifically concerns a sampling device which is suitable for procuring a specimen from a particular, designated location within a lake, stream, or other body of water for purposes of testing the composition or content.

BACKGROUND OF THE INVENTION

In the practice of certain disciplines concerned with the study of aquatic conditions and phenomena, sampling the water is frequently conducted for purposes of testing or analyzing the specimen or the environment from which the specimen was obtained. For example, in oceanography, samples are taken to study the chemical composition of oceanic waters, in pollution control, specimens are obtained and analyzed for purposes of detecting abnormal amounts of pollutants, and in marine biology and ichthyology, specimens of the aquatic environment often yield information related to biologic investigations.

Particularly, there has been a need for a mechanical device that can procure a sample of the water or other liquid at a predetermined location that is remote from the operator of such device. Thus, it is frequently desirable to obtain specimens at a specific depth or at a distant horizontal location that may be inaccessible or which the operator may wish to leave uncontaminated by his presence or the presence of a large vessel.

There have previously been in use liquid samplers for obtaining samples at a given depth. As illustrated in U.S. Pat. to Langguth No. 3,302,464 and U.S. Pat. to Puthoff, et al., No. 4,004,463, the apparatus typically employed consists essentially of a container having a remotely operable valve and a line or cable for lowering the device to a desirable depth and retrieving the device after procurement of the sample. The valves previously employed are often complicated mechanical systems which are opened to permit liquid to enter the container when the device arrives at the appropriate depth and closed to prevent liquid from escaping from the container during retrieval. Due to the complexity of the valves and the plurality of functional elements therein, the proper operation of the devices is not assured. Devices having valves dependent upon gravitational forces for operation, such as in U.S. Pat. to Bodman, et al., No. 3,277,723, wherein a weighted messenger is lowered down the cable to trigger the valve, cannot reliably function if, for example, currents in the water alter the vertical orientation so as to thwart the proper functioning of gravitationally activated elements. Similarly, other sampling devices, as in the above noted patent to Langguth, require physical contact with the bottom of the body of water to trigger the valve. Such structures limit the utility of the device with respect to sampling at varied depths.

A particular need for an inexpensive, functionally simple sampling device has arisen in the area of sport and competitive fishing. As studies have found, the material and chemical content of the water in an outdoor reservoir or moving body of water will vary according to conditions of the internal and surrounding environment, such as the concentration of vegetation and the intensity of sunlight. Furthermore, it has been found that fish of various species prefer certain water conditions, and specifically, that bass tend to migrate to those waters that are closest to a chemical content which is slightly alkaline. Experimental results have shown that bass can be found more often in waters having a pH approaching 7.5 to 7.9. It has therefore become the practice among some fishermen to measure the pH of the area to be fished before devoting time to actual fishing.

Devices previously in use for measuring pH in lakes or streams have typically been expensive and inaccurate. The inaccuracy predominantly results from the location of the measuring device with respect to the area to be fished, as when, for example, the device consists of a meter having a probe which is attached to the fisherman's boat while the area to be fished is close to a bank, over a submerged bar, or in some other inaccessible location. Thus, a sampling device that could be cast to the area to be fished, remotely controlled by the fisherman, and operated at selected depths would fulfill the need for a sufficiently accurate means for testing water conditions.

A convenient method of accomplishing remote control at selected depths is the employment of the principles of drag forces resulting when a body is moved through a fluid. As illustrated for example in the above noted patent to Puthoff, et al. and U.S. Pat. to Quist No. 2,615,340, the principle has been applied to sampling devices to operate a valve opening to the container. Thus, a quick pull on the line will impart motion to the device, induce a drag force in the opposite direction to that in which the line is pulled, and open the valve to permit ingress of liquid. The previous devices, however, typically employ a complex valve mechanism which is not amenable to consistent, proper, and reliable functioning. Furthermore, the manner in which these particular devices operate would appear to not permit the casting of the devices as is done in sport fishing, since triggered valves and weighted members would possibly be subject to premature operation upon casting or upon impact with the surface of the water.

It is accordingly an object of the present invention to provide a liquid sampling device that is suitable for obtaining a specimen from a large volume of the liquid and in a designated location therein.

Another object of the present invention is to provide a sampling device that is remotely operated and which is not dependent upon depth or gravitational conditions for operation. In this connection, it is also an object of this invention to provide an inexpensive device having a mechanically simple valve that permits consistent, workable performance.

It is a further object of the present invention to provide a sampling device that can be used in fishing to test the chemical composition of the area to be fished, where by casting the device to the area, the device can be operated from the remote location of the fisherman.

SUMMARY OF THE INVENTION

These and other objects and advantages of the present invention are achieved in the embodiment illustrated herein by the provision of a sampling device which comprises a first and second receptacle each having an open end and disposed with respect to each other so as to define a closed container and for relative movement between an open and closed position. Ports extend through the wall of at least one of the receptacles so that the exterior liquids can enter the container.

When the receptacles are in their open position, the ports communicate with the interior of the container, and when the receptacles are in their closed position, the ports are shut. A line is also attached to the device and mounted to the first receptacle so that the device can be pulled through the liquid. Liquid resistance means is provided for inducing a drag force on the second receptacle, and in the preferred embodiment such comprises a transverse external shoulder mounted adjacent the closed end of the second receptacle. The induced drag force causes the receptacles to move to their open position when the first receptacle is pulled through the liquid, and means is provided for biasing the receptacles to their closed position. Thereby, the rapid pulling of the device through the liquid causes the receptacles to move to their open position to admit a specimen of the liquid into the closed container.

BRIEF DESCRIPTION OF THE DRAWINGS

Some of the objects and advantages of the invention having been stated, others will appear as the description proceeds, when taken in connection with the accompanying drawings, in which:

FIG. 1 is a perspective view of the device embodying the features of the present invention, and wherein a line is attached to the device for remote operation;

FIG. 2 is a sectional side view illustrating the sampling device shown in FIG. 1;

FIG. 3 is a perspective view of the sampling device;

FIG. 4 is a sectional side view of the device, and illustrating the connection of a coiled spring between the receptacles; and FIG. 5 is an exploded perspective view of the sampling device.

DESCRIPTION OF THE ILLUSTRATED EMBODIMENT

Referring more specifically to the drawings, the illustrated embodiment of the sampling device is indicated generally at 10 and will be seen to include a first receptacle 12 having an open end 13. In the preferred embodiment, the first receptacle 12 is a tubular member having a circular cross section and which is closed at the end opposite the open end 13. A second receptacle 15, also having an open end 16, is disposed with respect to the first receptacle 12 to define a closed container. As shown in FIGS. 2 and 4, the second receptacle 15 in this embodiment would also comprise a tubular member which is closed at the end opposite the open end 16, and the circular cross section thereof would be such that the outside diameter of the second receptacle is slightly less than the inside diameter of the first receptacle 12. In this manner, the second receptacle 15 is telescopically disposed within the first receptacle 12 and in an opposing relationship to form a closed container between the closed ends of the receptacles. It is also contemplated that the disposition of the first and second receptacles could be reversed so that the first receptacle is telescopically disposed within the second receptacle.

The disposition of the receptacles 12 and 15 with respect to each other permits relative movement between open and closed positions. Thus, by telescoping therebetween, the receptacles 12 and 15 can slideably move between an open or extended position, as illustrated in FIG. 2, and a closed or contracted position, as shown in FIG. 4. In order to seal the receptacles 12 and 15 against one another, a rubber or fibrous "O" ring 18 is disposed in an annular groove 19 within the closed end of the first receptacle 12. When the receptacles are moved together, the free edge 21 of the wall of the second receptacle 15 will move toward and contact the ring 18 to thereby prevent liquid from seeping out of or into the container. At the point of contact between the free edge 21 and the ring 18, the contracted or closed position of the receptacles 12 and 15 is defined.

To prevent rotational motion between the receptacles 12 and 15, a pin 23 is mounted to the second receptacle 15 and extends through a slotted aperture 24 in the first receptacle 12. The slotted aperture 24 and pin 23 also prevent the receptacles from disengaging from one another upon separation. As the receptacles are extended, the pin 23 will contact one end of the slotted aperture 24 thereby preventing further separation and defining the extended or open position as hereinafter further described. In the illustrated embodiment, the pin 23 comprises a screw threaded into the wall of the second receptacle 15 and extending outwardly therefrom and through the slotted aperture 24. The length of the slotted aperture 24 is sufficient to permit the receptacles to move to their closed position wherein the ring 18 and free edge 21 will abut.

For ingress of the exterior liquids into the container, port means extend through the wall of at least one of the receptacles 12 and 15, and in the preferred embodiment, the port means comprises a plurality of apertures 26 disposed through the wall of the first receptacle 12. The apertures 26 are located near the closed end of the first receptacle 12 so that when the receptacles are in their contracted position, the apertures are shut or closed by the wall of the second receptacle 15. As the receptacles 12 and 15 are separated, the wall of the second receptacle 15 telescopes past the apertures 26, as illustrated in FIG. 2, thereby opening the apertures to communicate with the interior of the container. When the receptacles 12 and 15 are positioned so that the free edge 21 of the second receptacle 15 has cleared the apertures 26 and the apertures are unobstructed, liquid will freely flow into the interior of the container. In this position, the extended or open position is defined and the pin 23 will contact the end of the slotted apertures 24 to prevent further extension.

The apertures 26 are located on the first receptacle 12 in a spaced relationship circumferentially around the perimeter thereof. In this manner, each aperture is substantially diametrically opposite another aperture, and the escape of gases from the container when liquids enter therein is facilitated.

Means for attaching a line 28 to the sampling device 10 is also provided, and includes a screw member 29 threaded into the closed end of the first receptacle 12. An eye 30 in the projecting end of the screw member 29 receives the line 28 which is then properly secured by knotting or otherwise. Alternatively, a hook 31 commonly used by sport fishermen can be used to link the line 28 and screw member 29. The opposite end of the line 28 may be connected to a conventional reel for retrieval of the device. Similarly, a rod may be used in combination therewith for casting the device 10 as hereinafter described.

The point of attachment of the line 28 to the device 10 permits the operator to pull the device through the liquid and in a direction corresponding to that of slideable movement of the receptacles 12 and 15. In order to cause the receptacles 12 and 15 to move to their extended position when the operator pulls the line, liquid resistance means is provided for inducing a drag force on the second receptacle 15. As illustrated in the preferred embodiment, the liquid resistance means comprises a transverse external shoulder 34 mounted to the closed end of the second receptacle 15. The shoulder 34 increases the surface area of the second receptacle 15 perpendicular to the flow of liquid past the device. Thereby, when the line 28 is rapidly pulled, the second receptacle 15 resists the motion imparted, while the first receptacle 12, which is positively attached to the line, travels the distance drawn by the line. When the frictional forces between the receptacles 12 and 15 and the elastic forces hereinafter described are overcome by the drag forces, the receptacles separate to their extended position to admit a specimen of the liquid into the container. In other embodiments, for example those having the first receptacle disposed within the second receptacle, the shoulder can be located in any convenient position along the length of the second receptacle.

To urge the receptacles 12 and 15 to their contracted position, biasing means is interconnected between the receptacles. In the illustrated embodiment, the biasing means comprises three biasing elements such as coil springs 36, each of which is hooked to the first receptacle 12 at pins 37 and connected to the second receptacle 15 through eyes 38. The cumulative strength of the springs 36 is sufficient to maintain the receptacles 12 and 15 in their contracted position when the device is stationary, during slow movement through the water as for retrieval, and upon impact with the surface of the water when the device is cast. Yet, the springs 36 have sufficient elasticity to permit the receptacles to separate when rapid motion is imparted. A screw member 40 is also threaded into the closed end of the second receptacle 15 to provide means for attaching a weight 41 to the receptacle. Thereby, the separation of the receptacles and the ability to cast the device can be facilitated by the addition of appropriate amounts of weight.

The receptacles 12 and 15 are constructed from any suitable material, and in the illustrated embodiment a molded plastic or synthetic resin, which yields a relatively rigid composition, has been used. The shoulder 34 and second receptacle 15 are molded into an integral structure, and the receptacles 12 and 15 constructed from a clear plastic so that the contents of the container can be viewed. Thus, indicia means 43 is included for gauging or measuring the volume of liquid contained in the device, whereby testing of the liquid can be conducted within the container or the measured contents can be removed.

In use, the empty device 10 is attached to a line 28 through the eye 30 of the screw member 29. A weight 41 is also attached to the screw member 40 at the opposite end of the device if prior experience has shown such is required. The assembly including the weight 41 and sampling device 10 is then cast to the area from which the specimen is to be obtained, and a float or measured line can be used to position the device at the desired depth. When the device is properly positioned, a rapid pull on the line will cause the receptacles 12 and 15 to move to their extended position as explained above, whereupon the liquid will fill the container. The device is then slowly retrieved by drawing in the line. The strength of the springs 36 will retain the receptacles in their contracted position during retrieval so that undesired liquid will not enter the container.

Upon the return of the device to the operator, the amount of liquid contained therein is noted and experimental results obtained. The liquid can be emptied into another container by manually separating the receptacles 12 and 15 and pouring the liquid therefrom through the apertures 26. Alternatively, a substance, such as a conventional mixed indicator, is added to the container through the apertures 26 to observe the results, such as color changes which indicate pH. After emptying the container, the device is immediately available for subsequent reuse.

In the drawings and specification, there has been set forth a preferred embodiment of the invention, and although specific terms are employed, they are used in a generic sense only and not for purposes of limitation.

That which is claimed is:

1. A sampling device for procuring a specimen of liquid from a remote location within a body of the liquid and comprising
    a first receptacle having an open end;
    a second receptacle having an open end and disposed with respect to said first receptacle to define a closed container and for relative movement between an open position and closed position,
    port means extending through the wall of at least one of said receptacles for ingress of exterior liquids and communicating with the interior of the container when said receptacles are in their open position and being shut when said receptacles are in their closed position;
    means for attaching a line to the device and mounted to said first receptacle;
    means for biasing said receptacles to their closed position; and
    liquid resistance means for inducing a drag force on said second receptacle to cause said receptacles to move to their open position against the resistance of said biasing means when said first receptacle is rapidly pulled through the liquid by the line and thereby to admit a specimen of the liquid into the closed container.

2. A sampling device as defined in claim 1 wherein said first and second receptacles are tubular and are disposed in a telescoping relationship.

3. A sampling device for procuring a specimen of liquid from a remote location within a body of the liquid and comprising
    a first tubular member having a closed end;
    a second tubular member having a closed end and telescopically disposed with respect to said first member to define a closed container and for relative slideable movement between an extended position and a contracted position;
    port means disposed in the wall of at least one of said members and communicating with the interior of the container for ingress of exterior liquids thereinto when said members are in their extended position and being closed when said members are in their contracted position;
    means for attaching a line to said first member;
    liquid resistance means for inducing a drag force on said second member when said first member is rapidly pulled through the liquid by the line; and
    means for biasing said members to their contracted position, whereby said resistance means will oppose the flow of liquid past the device when said first member is pulled and thereby cause said members to separate to their extended position and admit a specimen of the liquid into the closed container.

4. A sampling device as defined in claim 3 wherein said liquid resistance means comprises a transverse external shoulder mounted adjacent the closed end of said second member.

5. A sampling device as defined in claim 4 wherein said means for attaching a line to said first member is mounted adjacent the closed end of said first member.

6. A sampling device as defined in claim 3 wherein said port means comprises a plurality of apertures in the wall of one of said members which are closed by the wall of the other of said members when said members are in their contracted position and opened when said members are moved to their extended position.

7. A sampling device as defined in claim 6 wherein some of said apertures are located substantially diametrically opposite the other of said apertures to facilitate the escape of gases from the container when liquids enter therein.

8. A sampling device as defined in claim 3 wherein said means for biasing said members to their contracted position comprises at least one biasing element coupled between said members so that said members are maintained in their contracted position when the device is stationary.

9. A sampling device as defined in claim 8 wherein said device further comprises means for attaching a weight adjacent the closed end of said second member to facilitate the separation of said members to their extended position when said first member is pulled through the liquid.

10. A sampling device as defined in claim 3 wherein said tubular members have a circular cross section.

11. A sampling device as defined in claim 3 wherein said device further includes indicia means for gauging the amount of liquid contained in the device after procurement of a specimen.

12. A sampling device as defined in claim 3 wherein the wall of one of said members has a slotted aperture, and the device further includes a pin mounted to the other of said members and extending through said slotted aperture so that rotational motion between said members is prevented and so that the extended position is defined upon contact of said pin with one end of said slotted aperture.

13. A sampling device for procuring a specimen of liquid from a remote location within a body of the liquid and comprising a first tubular member having a closed end and an open end;

a second tubular member having a closed end and an open end and telescopically disposed within said first member in an opposing relationship to define a closed container and so as to permit relative slideable movement therebetween;

means for limiting the relative sliding movement of said first and second tubular members to movement between an extended position and a contracted position;

port means disposed in the wall of at least one of said members and communicating with the interior of the container for ingress of exterior liquids thereinto when said members are in their extended position and being closed when said members are in their contracted position;

means for attaching a line to the device and mounted adjacent the closed end of one of said members;

a transverse external shoulder mounted to the other of said members; and biasing means interconnected between said first and second members for urging said members to their contracted position, whereby said shoulder will resist the flow of liquid parallel to the direction of movement of the device when it is pulled through the liquid by the line and whereby said shoulder will cause said members to separate to their extended position by the resistance to liquid flow and admit a specimen of the liquid into the closed container.

* * * * *